(12) United States Patent
Nakagami et al.

(10) Patent No.: US 6,855,127 B2
(45) Date of Patent: Feb. 15, 2005

(54) NEEDLE ASSEMBLY

(75) Inventors: Hiroyuki Nakagami, Osaka (JP); Satoshi Kamimura, Osaka (JP)

(73) Assignee: Nipro Corporation, Osaka (JP)

( * ) Notice: Subject to any disclaimer, the term of this patent is extended or adjusted under 35 U.S.C. 154(b) by 386 days.

(21) Appl. No.: 10/053,915

(22) Filed: Jan. 24, 2002

(65) Prior Publication Data

US 2002/0099341 A1 Jul. 25, 2002

(30) Foreign Application Priority Data

Jan. 25, 2001 (JP) ........................................ 2001-016916
May 17, 2001 (JP) ........................................ 2001-147372

(51) Int. Cl.[7] .............................................. A61M 5/00
(52) U.S. Cl. ...................................... 604/110; 604/187
(58) Field of Search ................................ 604/110, 187, 604/192, 198, 240–247, 263

(56) References Cited

U.S. PATENT DOCUMENTS 5,466,223 A * 11/1995 Bressler et al. ............. 604/198
5,672,161 A    9/1997 Allen et al. ................. 604/263

FOREIGN PATENT DOCUMENTS

| JP | 3-234264 A  | 10/1991 |
| JP | 6-63050 U   | 9/1994  |
| JP | 8-732 A     | 1/1996  |
| JP | 2739840 B2  | 1/1998  |
| JP | 10-127767 A | 5/1998  |
| JP | 2974299 B2  | 9/1999  |

* cited by examiner

Primary Examiner—Manuel Mendez
(74) Attorney, Agent, or Firm—Kubovcik & Kubovcik

(57) ABSTRACT

A needle assembly comprising a needle, a needle hub in which the needle is secured at a distal end portion of the needle hub, a protector having an elongated rod-shaped main body and a needle tip protection part provided on the distal end of the main body for sliding on the needle, and a cylindrical hub cover having an inner channel provided on the distal end of the needle hub. The needle hub and the hub cover each have such a shape as to form a side hole when the needle hub and the hub cover are integrally joined, and the protector main body moves to the distal end or the proximal end while inserted in the side hole.

12 Claims, 6 Drawing Sheets

NEEDLE ASSEMBLY

TECHNICAL FIELD OF THE INVENTION

This invention relates to a needle assembly and, more specifically, to a needle assembly having a mechanism for preventing a medical needle to which blood or the like is adhered after use from accidently piercing a human body.

BACKGROUND OF THE INVENTION

Heretofore, a medical needle such as an injection needle has included a metal needle, a hub provided on a proximal end of the metal needle for fixing the metal needle, and a cap capable of fitting on the hub and covering a tip of the metal needle to prevent accidental piercing. The injection needle is used with the cap covering the tip of the injection needle being detached. Then, after use, the tip of the injection needle contaminated with a patient's blood or body fluid is covered with the cap to prevent an operator, a patient, a person who discards the needle or the like from being injured by accidental contact with the sharp tip and from acquiring diseases such as hepatitis or various other kinds of infectious diseases.

Conventional injection needle assemblies capable of protecting a used injection needle safely and easily include such assemblies that a cylindrical shield provided so as to cover an outer cylinder of a syringe is slid toward a distal end of an injection needle to protect the injection needle (Japanese Patent Application Laid-Open Nos. 342200/1999, 319090/1999, 127765/1998, etc.); a shield hinged at a hub provided on a proximal end of an injection needle is rotated relative to the injection needle to protect the injection needle (Japanese Patent Application Laid-Open Nos. 57005/1999, 248930/1998 and 113392/1998); and a distal end of an injection needle is protected by a shield movable along the injection needle in the axial direction of the injection needle (Japanese Patent Application Laid-Open Nos. 206204/1996, 250898/1995, 148176/1995, etc.).

Such conventional injection needle assemblies require use of both hands of an operator for operation. The operation is that the operator has to hold a medical instrument using one hand and move the shield to protect the injection needle using the other hand. Further, since any of the injection needle assemblies is large in size, the injection needle assemblies generate an extremely large amount of waste.

On the other hand, one hand-operable injection needle assemblies have been developed in view of the problems described above (Japanese Patent Application Laid-Open No. 234264/1991, Japanese Utility Model Application Laid-Open No. 63050/1994 and Japanese Patent Nos. 2739840 and 2974299). In the one hand-operable injection needle assemblies, a needle guard capable of protecting at least the distal end of the injection needle is provided parallel to the axial direction of the injection needle and the proximal end of the needle guard extends as far as the injection cylinder. After use of the injection needle assemblies, the proximal end of the needle guard is pushed by any of the fingers of a syringe-holding hand to move the needle guard toward the distal end of the injection needle and the distal end of the injection needle is protected. Since such injection needle assemblies do not require both hands for operation, the operator can easily protect the injection needle.

However, in the one hand-operable injection needle assemblies described above, it is necessary, in order to provide the needle guard, to form an additional hole for insertion of the needle guard. The hole is formed by forming another hole, in addition to a hole for inserting an injection needle, in a needle hub or providing a separate member having a hole on the needle hub in the injection needle assemblies. In that case, it is difficult to assemble the needle guard with the needle hub.

Further, in the injection needle assemblies having a needle guard made of a hard resin (Japanese Utility Model Application Laid-Open No. 63050/1994, Japanese Patent Nos. 2739840 and 2974299), the needle guard is not adjacent to the injection needle but is positioned parallel to the injection needle and spaced apart from the injection needle, so that the size of such assemblies is large and the assemblies are difficult to use. Besides, in the injection needle assemblies described above, since the needle guard is provided on the assemblies at the distal side of the needle hub, the total length of the needle is made longer and it is difficult to pierce the needle into a patient.

Further, an injection needle assembly having a needle guard made of a flexible resin (Japanese Patent Application Laid-Open No. 234264/1991) has a mechanism in which a notch is formed along the axial direction of the needle guard and the injection needle is accommodated in the needle guard through the notch of the needle guard when the needle guard is slid along the injection needle to the distal end. However, it is necessary to form the notch in the needle guard to provide the mechanism described above, and the process for producing the mechanism requires a complicated step. In addition, the needle guard has to be considerably flexible and it is difficult to push the proximal end position of the needle guard to slide the needle guard on the injection needle using one hand when protecting the injection needle.

In view of the foregoing situations, an object of this invention is to provide a needle assembly which is compact in shape and easy to assemble, and can be operated using one hand.

SUMMARY OF THE INVENTION

Intense studies have been carried out by the inventors in order to solve the problems described above. As a result, it has been found that a needle assembly which is compact in shape and easy to assemble, and can be operated using one hand can be obtained by using a structure in which an opening is provided on the lateral side of a needle hub and a protector is moved along the needle, and the present invention was completed.

That is, this invention relates to a needle assembly comprising a hollow needle having a sharp needle tip at a distal end of the needle; a needle hub in which the needle is secured at a distal end of the needle hub and having an inner lumen in communication with the inside of the needle; a protector having an elongated rod-shaped main body and a needle tip protection part which is a tubular cylindrical member provided on the distal end of the main body of the protector for sliding on the needle; a cylindrical hub cover having an inner channel accommodating the needle and the needle tip protection part at the inside and provided on the distal end of the needle hub; the needle hub and the hub cover each having such a shape as to form a side hole providing communication between the outside and the inner channel of the hub cover when the needle hub and the hub cover are joined; and wherein the main body of the protector is positioned in the side hole and is capable of moving to the distal end or the proximal end of the needle while positioned in the side hole.

The needle used for the needle assembly according to this invention includes medical needle products such as an injection needle, a blood sampling needle, an indwelling needle, a needle for use in an infusion liquid set and a winged needle.

DESCRIPTION OF THE DRAWINGS

Referring to the preferred embodiments and attached drawings, needle assemblies of the present invention will hereinafter be described. However, the present invention is not limited to these embodiments.

DETAILED DESCRIPTION OF THE INVENTION

Figure 1:
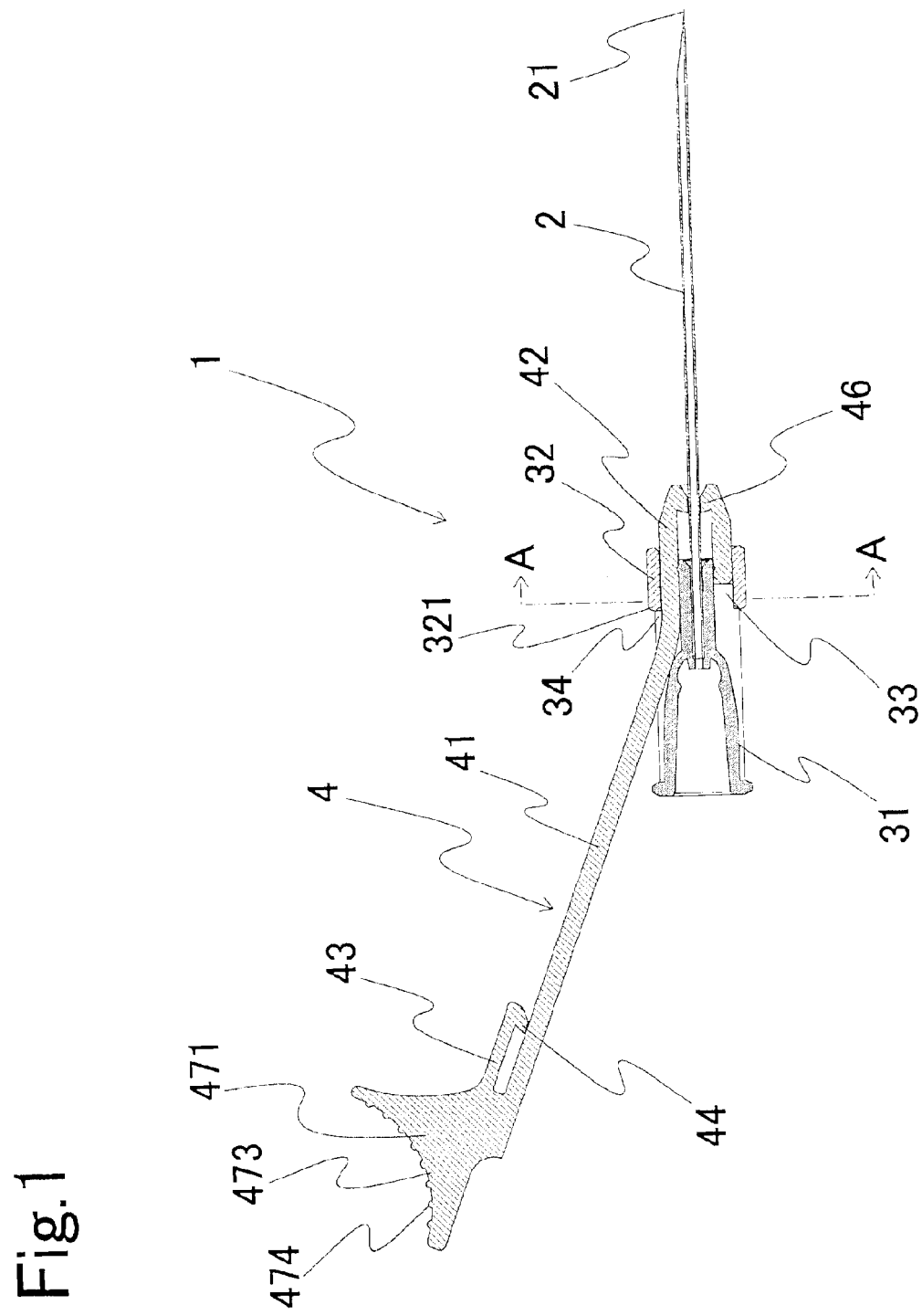
FIG. 1 is a longitudinal cross sectional view showing an embodiment of an injection needle assembly according to this invention in a state that the needle tip has not been protected.

In a needle assembly 1 according to this invention, the term "distal end" means the end with which a patient or the like is pierced (rightward in the drawing) and the term "proximal end" means the end opposite the distal end (leftward in the drawing). Further, although not illustrated, the injection needle assembly 1 according to this invention is used by being connected to a syringe, a connector, an infusion liquid tube or the like at a proximal end of the injection needle assembly 1.

A needle 2 used in this invention is a hollow tube and has a sharp needle tip 21 formed at the distal end portion thereof. The needle tip 21 has a bevel for reducing piercing resistance. The material for the needle 2 can include metals such as stainless steel, aluminum or titanium, and alloys of such metals.

As shown in FIG. 1, a needle hub 31 is fixed to the proximal end of the needle 2. The method for fixing the needle 2 and the needle hub 3 can include adhesion using an adhesive, fusion by heat and so forth. The needle hub 31 is a hollow tubular body having an inner lumen in communication with an inside of the needle 2. The inner lumen of the needle hub 31 is formed in a tapered shape in which an inner diameter is increased toward the proximal end. A hub cover 32 which is also a hollow tubular body is provided on the distal end of the needle hub 31. The hub cover 32 has an inner channel 33 penetrating from the distal end to the proximal end. A diameter of the inner channel 33 is set somewhat larger than an outer diameter of a protector 4 which is described later such that the needle 2 and the protector 4 are capable of being accommodated in the inner channel 33. The length of the hub cover 32 is not particularly limited so long as it is of such an extent that a portion of the protector 4 is capable of being accommodated in the hub cover 32 and does not cause problems when forming a side hole 34 which is described later. As a material for the needle hub 31 and the hub cover 32, hard materials such as polycarbonate, acrylonitrile-butadiene-styrene copolymer, polystyrene, polyethylene or polypropylene are preferably used.

Figure 2:
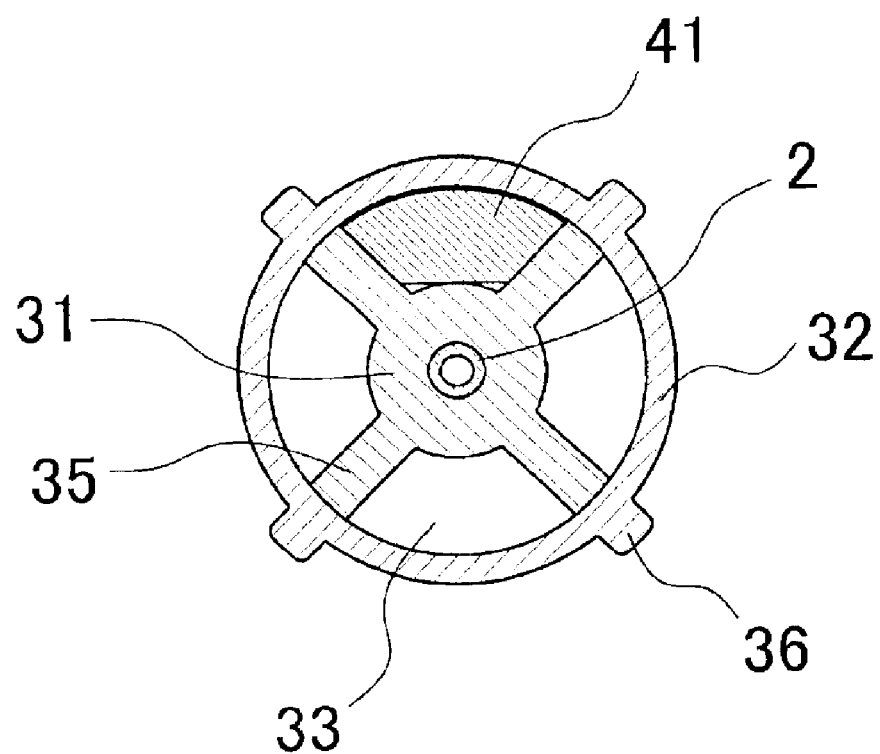
FIG. 2 is a transverse cross sectional view taken along line A—A of the injection needle assembly shown in FIG. 1.

At least one rib 36 as shown in FIG. 2 may be provided on an outer surface of the hub cover 32 for fixing a cap (not illustrated) to the hub cover 32. The cap covers the needle 2 and the needle tip 21 to protect the needle 2 and the needle tip 21 before the injection needle assembly 1 is used.

The needle hub 31 and the hub cover 32 have such a shape as to form a side hole 34 capable of providing communication between the outside and the inner channel 33 of the hub cover 32 when integrally joined. The method for joining the needle hub 31 and the hub cover 32 can include adhesion using an epoxy resin or UV-curable adhesive, welding by supersonic welding or the like. In the case that the needle hub 31 and the hub cover 32 are integrally molded, a method for forming the side hole 34 is a method of cutting or the like, or a method for providing a hinge on the hub cover 32 so that a portion of the hub cover 32 is capable of opening and closing. Further, there is no particular limitation on the shape or size of the side hole 34 so long as it is somewhat larger than a protector main body 41 which is described later.

Referring to FIG. 2, an embodiment of a method for joining the needle hub 31 and the hub cover 32 will hereinafter be described. The hub cover 32 is a tubular body such as a cylinder having the inner channel 33. The needle hub 31 has four ribs 35 arranged radially on an outer surface of the needle hub 31. The size of the any of the ribs 35 is a size of such an extent that the ribs 35 touch a wall of the inner channel 33 when the needle hub 31 is inserted into the inner channel 33 of the hub cover 32. The needle hub 31 and hub cover 32 are joined integrally when the ribs 35 are joined to the hub cover 32. In the case that the inner channel 33 of the hub cover 32 is divided into four channels by the ribs 35 as shown in FIG. 2, the protector main body 41 which is described later is arranged in one of the channels.

The protector 4 as one of constituent elements of the injection needle assembly 1 according to this invention has an elongated rod-shaped main body 41 and is formed of materials having moderate flexibility. Such materials are polypropylene, polycarbonate, acrylonitrile-butadiene-styrene copolymer, polystyrene, polyethylene, polyacetal and the like. The protector main body 41 is capable of moving to the distal end or the proximal end of the injection needle assembly 1 in a state being inserted into the side hole 34.

There is no particular limitation on the cross sectional shape of the protector main body 41. However, the cross sectional shape of the protector main body 41 preferably conforms to a shape of the side hole 34 in order to minimize friction at the time of being inserted in the side hole 34. For example, in a case where the shape of the side hole 34 is square, the cross sectional shape of the protector main body 41 is preferably also square. In this case, the cross sectional shape of the protector main body 41 may be a rectangular flat plate shape. Further, in the case that the inner channel 33 of the hub cover 32 is divided into four channels by the ribs 35, the cross sectional shape of the protector main body 41 is preferably similar to the shape of one of the channels.

A needle tip protection part 42 capable of accommodating the needle tip 21 of the needle 2 is formed on the distal end of the protector main body 41. The needle tip protection part 42 is a tubular cylindrical member in which the needle 2 is inserted therein. An inner diameter of the needle tip protection part 42 is set somewhat larger than an outer diameter of the needle 2 such that the needle tip protection part is slidable toward the distal end or the proximal end on the needle 2.

Figure 3:
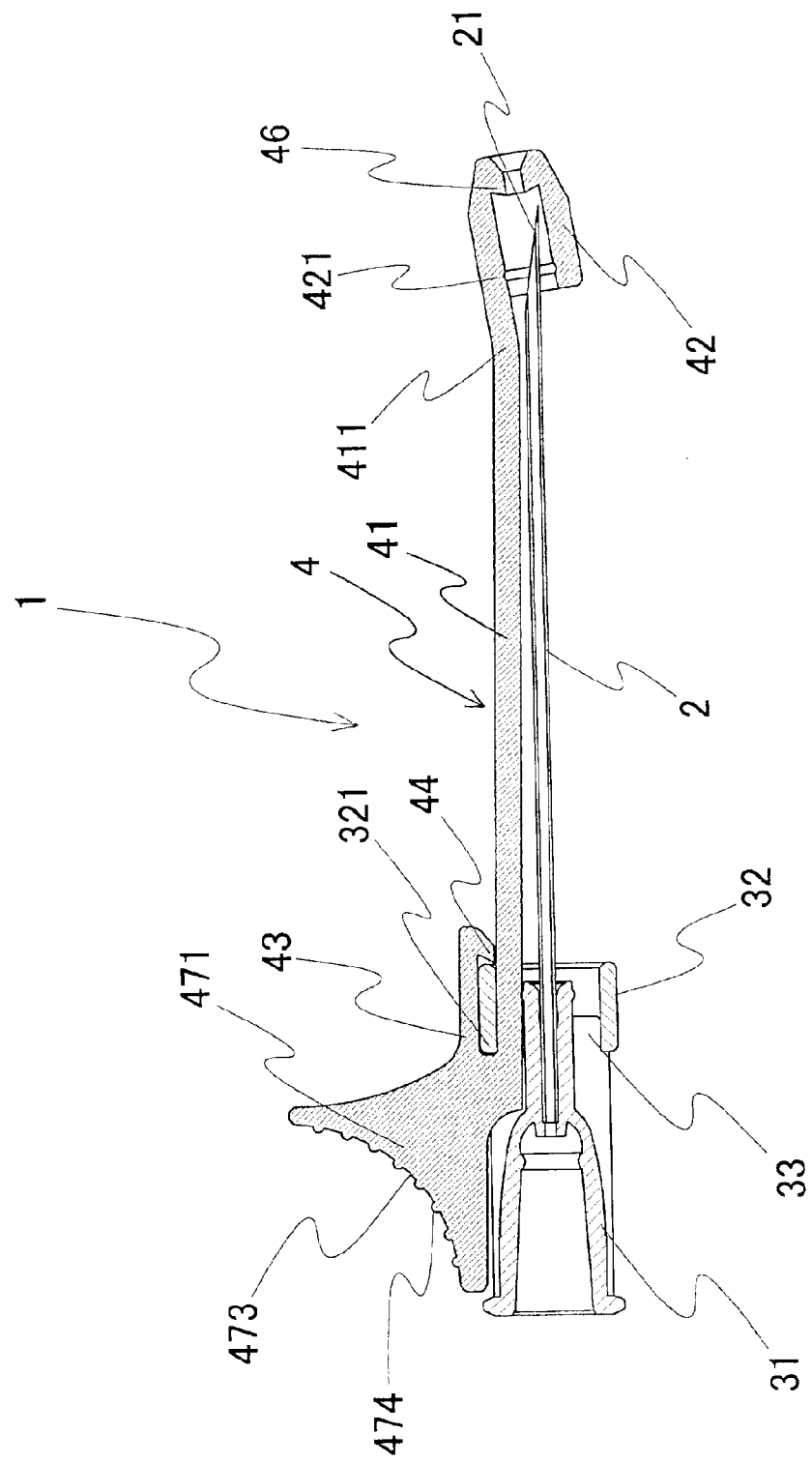
FIG. 3 is a longitudinal cross sectional view of the injection needle assembly shown in FIG. 1 in a state that the needle tip has been protected.
Figure 5:
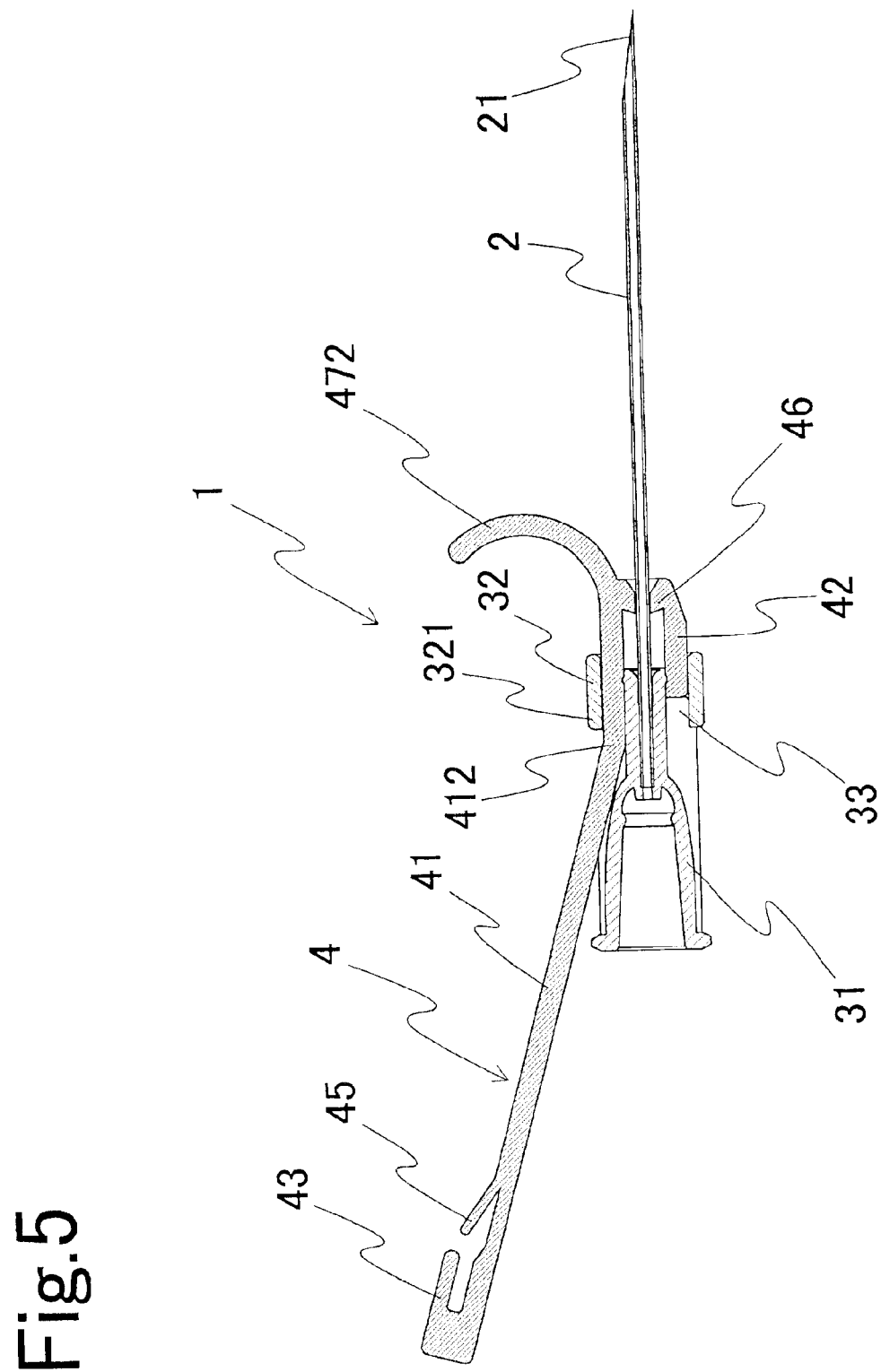
FIG. 5 is a longitudinal cross sectional view showing another embodiment of an injection needle assembly according to this invention in a state that the needle tip has not been protected.
Figure 6:
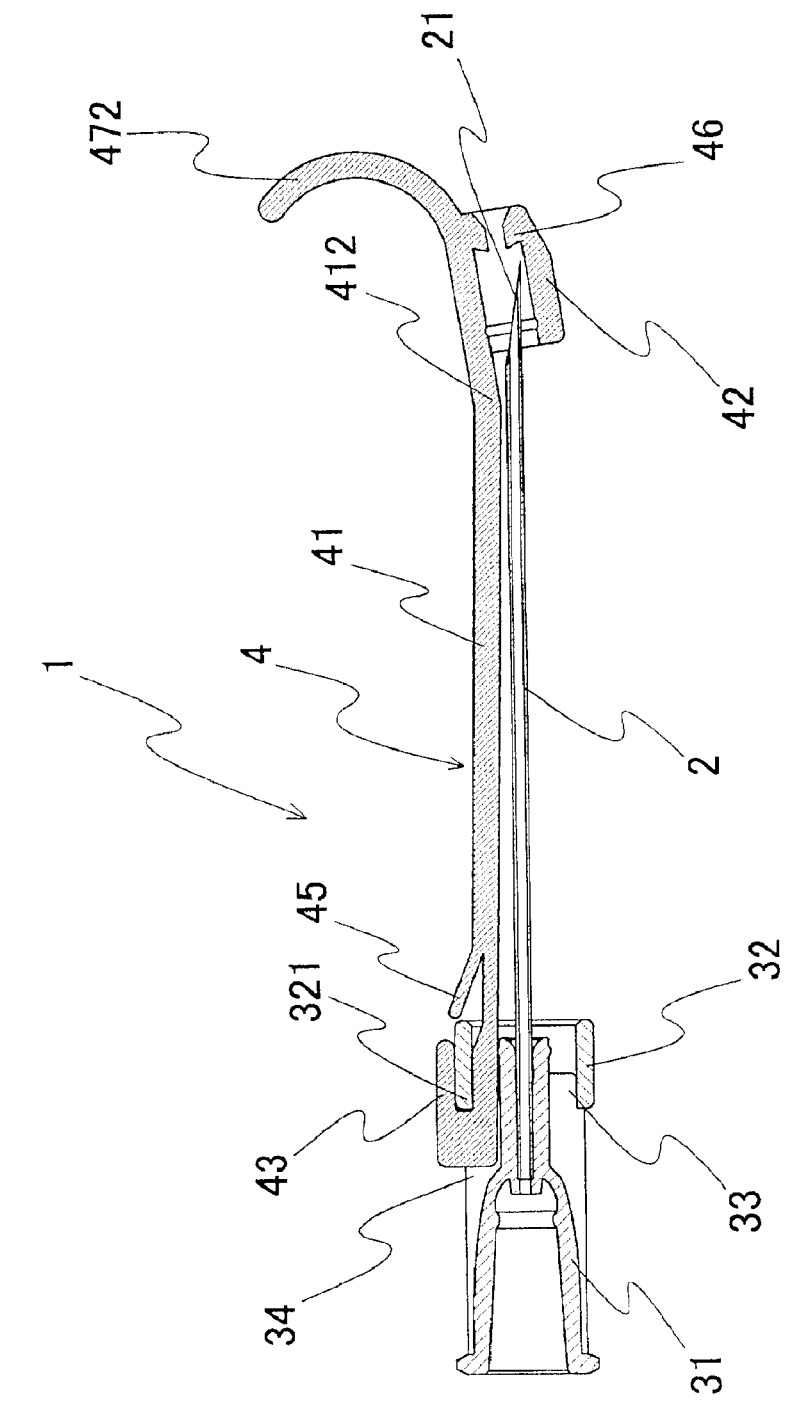
FIG. 6 is a longitudinal cross sectional view of the injection needle assembly shown in FIG. 5 in a state that the needle tip has been protected.

Before use and during use of the injection needle assembly 1, that is, before protection of the needle tip 21, the protector 4 is positioned so that the needle tip protection part 42 is arranged in the inner channel 33 of the hub cover 32, as shown in FIG. 1 and FIG. 5. After use of the injection needle assembly 1, that is, upon protecting the needle tip 21, the protector 4 is slid toward the distal end by pushing the protector 4 toward the distal end with any of fingers of a hand holding the injection needle assembly 1. After that, as shown in FIG. 3 and FIG. 6, the protector 4 is positioned at a position where the needle tip 21 is accommodated in the needle tip protection part 42.

A first positioning means is preferably provided on the injection needle assembly 1 so as to position the protector 4 in a position before protection of the needle tip 21. The first positioning means is a means for positioning the protector 4 so that the protector 4 does not move easily toward the distal end or the proximal end from the position in which the needle tip protection part 42 is arranged in the inner channel 33 of the hub cover 32 as shown in FIG. 1.

Figure 4:
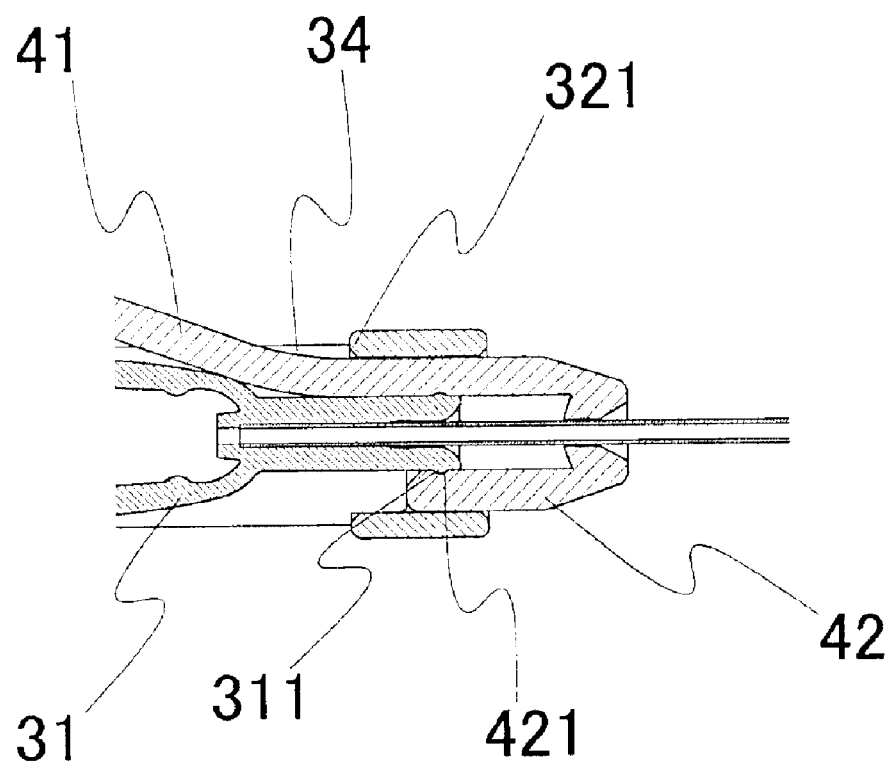
FIG. 4 is an enlarged cross sectional view of a distal end portion of needle hub 31 in the injection needle assembly shown in FIG. 1.

The first positioning means is, for example, a means for engaging a projecting portion 311 provided on the outer surface of the distal end portion of the needle hub 31 with a depressed portion 421 provided on the inner surface of the needle tip protection part 42 of the protector 4 as shown in FIG. 4. The first positioning means may also be a means for engaging a depressed portion provided on the outer surface of the distal end portion of the needle hub 31 with a projecting portion provided on the inner surface of the needle tip protection part 42 of the protector 4. Further, the first positioning means may be a means for only fitting the needle hub 31 with the needle tip protection part 42 without providing a projecting portion or a depressed portion.

Further, a second positioning means is preferably provided on the injection needle assembly 1 so as to position the protector 4 at a final position upon protecting the needle tip 21. The second positioning means is a means for positioning the protector 4 so that the protector 4 does not move easily toward the distal end or the proximal end from the position that the needle tip protection part 42 accommodates the needle tip 21 as shown in FIG. 3.

A means for preventing the protector 4 from moving toward the distal end and provided as a second positioning means includes, for example, an engaging arm 43 provided on the proximal end portion of the protector 4 for engaging with a side hole forming portion 321 of the hub cover 32 as shown in FIG. 3 and FIG. 6. In the case that a finger contact part 471 (described later) of the protector 4 is provided on the proximal end of the protector 4 as shown in FIG. 3, since the finger contact part 471 engages the side hole forming portion 321 of the hub cover 32, it is not necessary to provide the engaging arm 43 on the protector 4.

Further, a means of preventing the protector 4 from moving toward the proximal end and provided as a second positioning means includes, for example, a projection 44 which is provided on the distal end portion of the engaging arm 43 of the protector 4 and is projected inwardly for engaging with the distal end portion of the hub cover 32 as shown in FIG. 3. The means of preventing the protector 4 from moving toward the proximal end of the needle injection assembly 1 may also be a projection 45 which is provided on the protector main body 41 and is projected outwardly for engaging with the distal end portion of the hub cover 32 as shown in FIG. 6. Further, the second positioning means may be a projection 46 provided on the inner surface of the distal end portion in the needle tip protection part 42 of the protector 4 for engaging with the needle tip 21 as shown in FIG. 3. However, in a case that the means for engaging the projection 46 with the needle tip 21 is provided, it is preferable that the means for engaging the projection 44 with the distal end portion of the hub cover 32 or engaging the projection 45 with the distal end portion of the hub cover 32 is also provided. Further, in a case that a gently curved portion 411 bent outwardly as shown in FIG. 3 or a bent portion 412 as shown in FIG. 5 is provided on the distal end portion of the needle tip protection part 42 of the protector 4, the projection 46 will surely engage with the needle tip 21.

As the second positioning means, it is preferable that at least one means selected from the means for preventing the protector 4 from moving toward the distal end and at least one means selected from the means for preventing the protector 4 from moving toward the proximal end are provided on the injection needle assembly 1.

A finger contact part is preferably provided on the protector 4 according to this invention so as to push the protector 4 to the distal end of the injection needle assembly 1 with any of fingers of a hand holding the injection needle assembly 1 upon protection of the needle tip 21. The finger contact part may be a finger contact part 471 provided on the proximal end portion of the protector 4 as shown in FIG. 1 and FIG. 3. The finger contact part may also be a finger contact part 472 provided on the distal end of the protector 4 as shown in FIG. 5 and FIG. 6 in a case where the length of the needle 2 is short, so long as it can be operated using one hand. There is no particular limitation on the shape of the finger contact part so long as it is a shape that is pressed or pushed easily with any of fingers of the hand holding the injection needle assembly 1. However, it is more preferable that an arcuate indentation 473 conforming to the shape of a finger is provided on a surface in which the finger is contacted as shown in FIG. 1 and FIG. 3. Further, a number of ribs 474 are preferably provided on the indentation for preventing a finger from sliding on the indentation 473 so as to make the operation of protecting the needle tip 21 easier.

An embodiment of a method for assembling the injection needle assembly 1 according to this invention will hereinafter be described. The needle tip 21 of the needle 2 fixed to the distal end portion of the needle hub 31 is inserted into the inner lumen of the needle tip protection part 42 of the protector 4 from the proximal side. The needle tip protection part 42 is then arranged on the outer surface of the distal end portion of the needle hub 31. Then, the needle tip 21 is inserted into the inner channel 33 of the hub cover 32 and the hub cover 32 is arranged on the outer surface of the needle tip protection part 42. In this case, since the protector 4 is fixed on the needle hub 31 by the first positioning means, there is no fear that the protector 4 can move easily toward the distal end or the proximal end. The injection needle assembly 1 according to this invention has a simple configuration which is described above and is easy to assemble.

A length of an exposed portion of an injection needle is decided in advance. In the case of a conventional injection needle assembly where the needle tip protection part is provided on the distal side from the needle hub, the total length of the needle is made longer to account for the length of the needle tip protection part, so that it is difficult to pierce the needle into a patient. However, in the case of the injection needle assembly 1 according to this invention, a portion of the needle tip protection part 42 of the protector 4 is arranged on the needle hub 3, and a total length of the needle 2 is not as long as the length of the needle of the conventional injection needle assembly. As a result, the needle 2 of the present invention is easy to pierce into a patient using one hand.

An embodiment of a method of using the injection needle assembly 1 according to this invention will hereinafter be described. As a general rule, when an operator pulls out the injection needle from a patient, the operator holds the injection needle assembly using one hand to pull out the needle and presses the place that was pierced with the needle on the skin of the patient with a gauze or the like using the other hand. In the case of using the injection needle assembly 1 in which the finger contact part 471 is provided on the proximal end portion of the protector 4 as shown in FIG. 1, shortly after the operator pulls out the needle 2 from the skin of the patient, the operator pushes the finger contact part 471 toward the distal side of the injection needle assembly 1 with any of fingers of the hand holding the injection needle assembly 1 and the needle tip 21 becomes accommodated in the needle tip protection part 42 of the protector 4.

On the other hand, in the case of using the injection needle assembly 1 in which the finger contact part 472 is provided on the distal end portion of the protector 4 as shown in FIG. 5, the operator pulls out the needle 2 from the skin of the patient while hooking any of the fingers, preferably, a thumb, of the hand pushing the place which was pierced with the needle on the skin of the patient, on the finger contact part 472, and the needle 2 is pulled out from the skin of the patient. Thereby, since the needle 2 becomes accommodated in the needle tip protection part 42 as well as the needle 2 is pulled out from the patient's body, there is little fear that the operator is pierced by the needle 2 and that the operator will be infected by a patient's body fluid adhered to the needle 2. Further, the injection needle assembly 1 as shown in FIG. 1 is capable of using the same method as that of the injection needle assembly as shown in FIG. 5, for accommodating the needle 2 in the needle tip protection part 42 as well as the needle 2 being pulled out of the patient body.

The injection needle assembly 1 according to this invention preferably has a cap (not illustrated) on the needle 2 to protect the needle tip 21 when the assembly has not been used as shown in FIG. 1 and FIG. 5. When the injection needle assembly 1 is used, the cap is detached.

The needle assembly according to this invention is capable of being used as a blood sampling needle assembly, an indwelling needle assembly or medical needle assemblies such as a needle for an infusion liquid set or a winged needle or the like, in addition to being used as the injection needle assembly described above. Any of the needle assemblies has the same basic structure and effect obtained therefrom as that of the injection needle assembly and wherein the first positioning means and the second positioning means are joined and provided on them accordingly.

EFFECTS OF THE INVENTION

Since the side hole is formed between the needle hub and the hub cover by themselves, and a protector made of a flexible resin is inserted through the side hole, the needle assembly according to this invention has no requirement of forming a hole for inserting the protector to a needle hub or a separate member on the needle hub. The size of the needle assembly according to this invention is not enlarged since the protector slides along the needle, and a needle assembly having a size which is easily used can be provided. Further, the needle assembly according to this invention is easy to assemble and the manufacturing step of the needle assembly is capable of being simplified. Therefore, the needle assembly according to this invention is not required to be provided with an extremely long needle and the needle tip can be easily protected using one hand.

What is claimed is:

1. A needle assembly comprising a hollow needle having a sharp needle tip at a distal end of the needle; a needle hub having a distal end in which the needle is secured and having an inner lumen in communication with the inside of the needle; a needle protector having an elongated rod-shaped main body and a needle tip protection part, said needle tip protection part being a tubular cylindrical member provided on a distal end of said main body for sliding on the needle; a cylindrical needle hub cover provided on the distal end of the needle hub and having an inner channel for accommodating the needle and the needle tip protection part therein; the needle hub and the needle hub cover each having such a shape as to form a side hole providing communication between the outside of said assembly and the inner channel of the needle hub cover when the needle hub and the needle hub cover are joined; wherein said main body of the protector is positioned in said side hole and is movable along the needle toward the distal end or the proximal end of the needle.

2. A needle assembly according to claim 1, wherein the needle protector is movable from a position where said needle tip protection part is arranged in the inner channel of the needle hub cover before protection of the needle tip to a position where the needle tip is accommodated in the needle tip protection part for protecting the needle tip.

3. A needle assembly according to claim 2, wherein said assembly includes a first positioning means for positioning and maintaining the protector in a position where the needle tip protection part is arranged in the inner channel of the needle hub cover before the needle tip is protected.

4. A needle assembly according to claim 3, wherein the first positioning means is a means for engaging the distal end portion of the needle hub with the needle tip protection part of the protector.

5. A needle assembly according to claim 4, wherein the first positioning means comprises a projecting portion or a depressed portion provided on an outer surface of the needle hub and a depressed portion or a projecting portion provided on an inner surface of the needle tip protection part of the protector for engaging with said projecting portion or said depressed portion, respectively, provided on the other surface of the needle hub.

6. A needle assembly according to claim 2, wherein said assembly includes a second positioning means for positioning and maintaining the protector in a position where the needle tip is accommodated in the needle tip protection part when the needle tip is protected.

7. A needle assembly according to claim 6, wherein the second positioning means comprises a means for engaging a proximal end portion of the protector with the needle hub cover.

8. A needle assembly according to claim 6, wherein the second positioning means comprises an engaging arm provided on the distal end portion of the protector for engaging with a side hole forming portion of the needle hub cover to prevent the protector from moving toward a distal end of said assembly, and a projection provided on the distal end portion of said engaging arm of the protector and projecting inwardly for engaging with a distal end portion of the needle hub cover to prevent the protector from moving toward a proximal end of said assembly.

9. A needle assembly according to claim 1, wherein a projecting portion or a depressed portion is provided on an outer surface of the distal end of the needle hub, a depressed portion or a projecting portion is provided on an inner surface of the needle tip protection part of the protector for engaging said projecting portion or the depressed portion, respectively, on the outer surface of the needle hub, an engaging arm is provided on a proximal end portion of the protector for engaging a side hole forming portion of the needle hub cover, and a projection is provided on a distal end portion of the engaging arm and is projected inwardly toward the needle hub cover for engaging the distal end portion of the needle hub cover.

10. A needle assembly according to claim 1, wherein a cap for protecting the needle tip is removably provided on said needle hub.

11. A needle assembly according to claim 1, wherein said needle protector is formed of a thermoplastic material having moderate flexibility.

12. A needle assembly according to claim 11, wherein said thermoplastic material having moderate flexibility is selected from the group consisting of polypropylene, polycarbonate, acrylonitrile-butadiene-styrene copolymer, polystyrene, polyethylene, and polyacetal.

* * * * *